US00PP19023P3

(12) United States Plant Patent
Bacon et al.

(10) Patent No.: US PP19,023 P3
(45) Date of Patent: Jul. 15, 2008

(54) PLUM TREE NAMED 'SUPLUMTHIRTYSIX'

(50) Latin Name: *Prunus salicina*
Varietal Denomination: Suplumthirtysix

(75) Inventors: Terry A. Bacon, Bakersfield, CA (US); David W. Cain, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 214 days.

(21) Appl. No.: 11/329,262

(22) Filed: Jan. 10, 2006

(65) Prior Publication Data

US 2007/0163011 P1 Jul. 12, 2007

(51) Int. Cl.
*A01H 5/00* (2006.01)

(52) U.S. Cl. ..... Plt./184
(58) Field of Classification Search ..... Plt./184
See application file for complete search history.

(56) References Cited

U.S. PATENT DOCUMENTS

PP2,747 P 6/1967 Garabedian
PP10,608 P 9/1998 Zaiger et al.

*Primary Examiner*—Annette H Para
(74) *Attorney, Agent, or Firm*—Knobbe, Martens, Olson & Bear, LLP

(57) ABSTRACT

A new and distinct variety of plum tree, *Prunus salicina* 'Suplumthirtysix' that is characterized by heavy and consistent production of late season large (70 mm) elongated fruit, often having a prominent tip. The flesh is amber-colored with a crisp, very juicy texture, aromatic flavor, high sugar content (19° brix), and low acidity. The fruit skin is reddish-black with a neutral flavor.

1 Drawing Sheet

Figure 1:
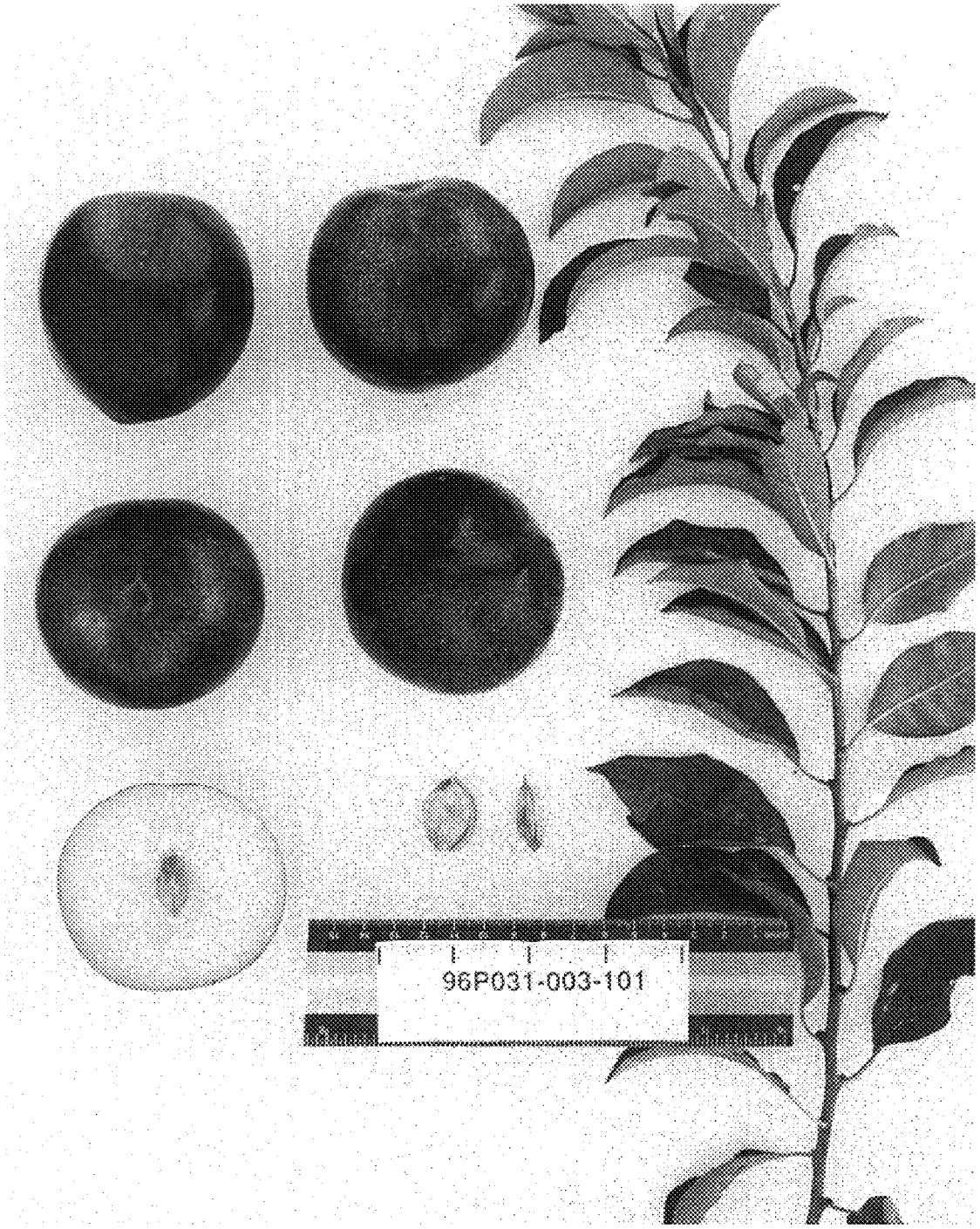

Latin name of the genus and species of the plant claimed: *Prunus salicina.*
Variety denomination: 'Suplumthirtysix'.

BACKGROUND AND SUMMARY OF THE INVENTION

This invention relates to the discovery and asexual propagation of a new and distinct variety of plum, *Prunus salicina* 'Suplumthirtysix'. The variety was originated by hybridization, being first hybridized and selected by David Cain. The new variety was first evaluated by David Cain and Terry Bacon near Wasco, Kern County, Calif. The new variety is characterized by heavy and consistent production of large (approximately 70 mm), reddish-black skinned, late season (late August) fruit. The fruit is elongated, often having a prominent tip. The fruit flesh is amber-colored with a crisp, very juicy texture, aromatic flavor, high sugar content (approximately 19° brix), and low acidity.

The seed parent of the new variety 'Suplumthirtysix' is breeding selection '90P-072' (unpatented) which was selected from a progeny of 'Queen Ann' (unpatented) crossed with pollen of 'Simka' (unpatented). The pollen parent the new variety 'Suplumthirtysix' is breeding selection '90P-070' (unpatented) which was selected from a progeny of 'Angeleno' (U.S. Plant Pat. No. 2,747) crossed with pollen of 'Simka.' The parent varieties were first crossed in March 1996, with the date of planting being February 1997, and the first flowering being in March 1999. The new plum variety was first asexually propagated by Terry Bacon near Wasco, Kern County, Calif. in 2001, by budding onto 'Flordaguard' (unpatented) rootstock.

The new variety 'Suplumthirtysix' is similar to its seed parent '90P-072' in most characteristics. However, the new variety 'Suplumthirtysix' can be distinguished from its seed parent in that its fruit ripens approximately two months earlier and is larger than the seed parent (approximately 70 mm compared to approximately 58 mm for '90-072').

The new variety 'Suplumthirtysix' can be distinguished from its pollen parent, '90P-070' in that the new variety ripens approximately three weeks earlier and has elongated fruit compared to round fruit of '90-070.'

The new variety 'Suplumthirtysix' most closely resembles the commercial plum variety 'Flavor Heart' (U.S. Plant Pat. No. 10,608), but may be distinguished from 'Flavor Heart' in that the new variety begins harvest approximately 10 days later and has skin color that is reddish-black compared to the black fruit skin of 'Flavor Heart.' The new variety 'Suplumthirtysix' ripens at about the same time as the comparable variety 'Angeleno' but has a larger fruit size (approximately 70 mm compared to approximately 58 mm for 'Angeleno.'

The new variety 'Suplumthirtysix' has been shown to maintain its distinguishing characteristics through successive asexual propagations by, for example, budding onto 'Flordaguard' rootstock.

BRIEF DESCRIPTION OF THE PHOTOGRAPH

The accompanying color photographic illustration shows typical specimens of the foliage and fruit of the present new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon the R.H.S. Colour Chart published by The Royal Horticultural Society, London, England.

The descriptive matter which follows pertains to 5 year old 'Suplumthirtysix' plants grown in the vicinity of Wasco, Kern County, Calif., during 2002, and is believed to apply to plants of the variety grown under similar conditions of soil and climate elsewhere.

TREE

General: (Measurements taken on five year old tree unless otherwise noted.).

*Size.*—Medium. Normal for most plum varieties. The tree reaches a height of approximately 3 meters including normal pruning.

*Vigor.*—Vigorous; growth of approximately 1.8 to 2 meters height the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Unknown, should be planted with another plum variety to ensure consistent production.

*Canopy density.*—Dense. Pruning is required to open tree vase shape, allowing more sunlight to center of tree.

*Hardiness.*—Hardy in all fruit growing areas of California. Winter chilling requirement is approximately 750 hours at or below 7.2° C.

*Disease resistance/susceptibility.*—No specific testing for relative plant disease resistance/susceptibility has been designed. Under close observation in area described in Wasco, Kern County, Calif., no particular plant/fruit disease resistance/susceptibility has been observed.

Trunk: (Measurements at 30 cm above soil line.).

*Diameter.*—Approximately 15 cm. Varies with soil type, fertility, climatic conditions and cultural practices.

*Surface texture.*—Smooth to slightly shaggy, increases with age of tree.

*Color.*—About Greyed-white 156A in exposed areas to Greyed-orange 164B in recesses. Becomes darker with age.

Branches: (Measurements at 90 cm above soil line.).

*Diameter.*—Ranges from approximately 4 to 6 cm.

*Surface texture.*—Smooth on first year wood, increasing roughness with tree age.

*Color.*—Branches vary from Greyed-green 197D to about Greyed-green 197B on exposed areas to about Greyed-orange 164C in recesses.

*Lenticels.*—Absent.

Flowering shoots: (Data taken in July at midpoint of current-season growth.).

*Diameter.*—Approximately 4 mm.

*Color.*—Topside: About Greyed-orange 165B. Underside: About Greyed-orange 165B with green background.

*Lenticels.*—Plentiful, very small. Size: About 1 mm. Color: About Greyed-orange 164C.

*Leaf buds.*—Shape: Broad obovate. Length: Approximately 2 mm. Width: Approximately 2 mm. Color: About Greyed-orange 177A.

*Flower buds.*—Shape: Broad obovate. Length: Approximately 2 mm. Width: Approximately 1.3 mm. Color: About Greyed-orange 177A. Number per node: Approximately 4.

FOLIAGE

Leaves: (Data taken in July on fully expanded leaf at midpoint of current-season growth.).

*Size.*—Average length: Approximately 90 mm. Average width: Approximately 36 mm.

*Thickness.*—Medium.

*Color.*—Upper surface: About Green 136B. Lower surface: About Green 138B.

*Form.*—Elliptic.

*Tip.*—Cuspidate.

*Base.*—Cuneate.

*Margin.*—Weakly crenate.

*Venation.*—Pinnately net veined.

*Vein color.*—About Yellow-green 147D.

*Surface texture.*—Smooth.

*Petiole.*—Average length: Approximately 16 mm. Average diameter: Approximately 2 mm. Color: About Yellow-green 147C with occasional highlights of about Greyed-red 179A on top surface.

*Stipules.*—Absent.

*Glands.*—Form: Globose where expressed, mostly eglandular on younger leaves. Number: Varies from approximately 2 to 4. Position: Opposite on upper portion of petiole. Average size: Approximately 0.8 mm by 0.8 mm. Color: About Greyed-red 179A.

FLOWERS

General: (Fully opened).

*Duration of bloom.*—Under temperature conditions near Wasco, Kern County, Calif., duration of flower bloom is about 12 days.

*Blooming period.*—First bloom: Mar. 9, 2002. Full bloom: Mar. 15, 2002.

*Average diameter.*—Approximately 24 mm.

*Aroma.*—Very slight.

Peduncle:

*Length.*—Approximately 8 mm.

*Diameter.*—Approximately 1 mm.

*Color.*—About Green 142A.

Petals:

*Number.*—5.

*Arrangement.*—Slightly overlapping.

*Length.*—Approximately 10 mm.

*Width.*—Approximately 8 mm.

*Shape.*—Obovate.

*Apex shape.*—Round.

*Base shape.*—Narrows at point of attachment.

*Color.*—About White 155.

*Surface texture.*—Smooth.

*Margins.*—Smooth.

Sepals:

*Number.*—5.

*Length.*—Approximately 4 mm.

*Width.*—Approximately 2.3 mm.

*Shape.*—Obovate.

*Color.*—About Green 142B.

*Surface texture.*—Smooth.

Stamens:

*Number.*—Approximately 23 to 27, averaging approximately 25.

*Average length.*—Approximately 6 mm.

*Filament color.*—About White 155.
*Anther color (just prior to dehiscence).*—About Greyed-yellow 160B.
*Pollen color.*—About Greyed-yellow 160B.

Pistil:
*Number.*—Usually one, occasionally two.
*Average length.*—Approximately 8 mm.
*Ovary diameter.*—Approximately 1 mm.
*Pubescence.*—None.
*Stigma extension.*—Stigma extends level with anthers.

FRUIT

General: (Data taken at firm-ripe stage on mature tree managed to obtain maximum quality under conditions stated above.).
*Harvest.*—Date of first pick: Aug. 14, 2002. Date of last pick: Aug. 25, 2002.

Size: (Under conditions typical of the San Joaquin Valley, Calif.).
*Length (stem end to apex).*—Approximately 75 mm.
*Diameter in line with suture plane.*—Approximately 70 mm.
*Diameter perpendicular to suture plane.*—Approximately 70 mm.
*Average weight.*—Approximately 195 gm.

Form:
*Viewed from apex.*—Rounded, nearly symmetrical.
*Viewed from side, facing suture.*—Rounded to elongated, nearly symmetrical, often with a prominent tip.
*Viewed from side, perpendicular to suture.*—Rounded to elongated, asymmetrical, often with a prominent tip.

Apex shape: Elongated, often with a prominent tip.
Stem-end cavity depth: Shallow.

Stem:
*Length.*—Approximately 8 mm.
*Diameter.*—Approximately 2 mm.
*Color.*—About Green 143C.

Skin:
*Thickness.*—Medium.
*Adherence to flesh.*—Tenacious.
*Surface texture.*—Smooth.
*Pubescence.*—None.
*Bloom.*—Moderate amount.
*Ground color.*—About Greyed-orange 163C.
*Overcolor.*—About Greyed-red 180A to about Greyed-purple 183A, not uniform.
*Taste.*—Mildly tart.

Flesh:
*Ripens.*—Evenly.
*Texture.*—Fine, firm, very juicy, crisp.
*Fibers.*—Few.
*Flavor.*—Sweet, with low acidity.
*Brix.*—Approximately 19 degrees.
*Juice.*—Plentiful.
*Aroma.*—Medium-high.
*Color.*—About Greyed-orange 164D.
*Pit cavity size.*—Approximately 28 mm in length. Diameter in line with suture plane: Approximately 19 mm. Diameter perpendicular to suture plane: Approximately 7 mm.
*Fruit use.*—Dessert. Market, local and long distance.
*Fruit shipping/keeping quality.*—Good. Holds well in cold storage for approximately 5 weeks and maintains good firmness and eating quality. Minimal bruising and scarring in packing and shipping trials.

Stone: (Measurements taken on dried stones.).
*Freeness.*—Clingstone.
*Size.*—Length: Approximately 28 mm. Diameter in line with suture plane: Approximately 19 mm. Diameter perpendicular to suture plane: Approximately 7 mm.
*Form (viewed from side).*—Elliptical oblong, slightly asymmetrical.
*Form (viewed from stem end).*—Oval, nearly symmetrical.
*Base shape.*—Narrows until stem attachment, then flattened for approximately 5 mm at stem attachment.
*Apex shape.*—Cuspidate to acuminate, with a sharp point.
*Surface.*—Irregularly furrowed near base. Lightly ridged toward base. Lightly pitted throughout.
*Halves.*—Nearly equal.
*Ridges.*—Typically 1 on each side of the suture. The ridges are small and narrow beginning at the base and extending throughout the length of the stone.
*Outgrowing keel.*—Partially developed.
*Tendency to split.*—None.
*Color.*—About Greyed-orange 165D when dried.

What is claimed is:

1. A new and distinct plum tree as herein described and illustrated.

* * * * *